United States Patent [19]

Bak

[11] Patent Number: Plant 7,727

[45] Date of Patent: Nov. 26, 1991

[54] GUZMANIA PLANT NAMED TWILIGHT

[75] Inventor: Gerardus J. Bak, Assendelft, Netherlands

[73] Assignee: Corn. Bak B.V., Netherlands

[21] Appl. No.: 513,881

[22] Filed: Apr. 24, 1990

[51] Int. Cl.[5] ..... A01H 5/00

[52] U.S. Cl. ..... Plt./88

[58] Field of Search ..... Plt./88

[56] References Cited

U.S. PATENT DOCUMENTS

P.P. 6,979 8/1989 Bullis, Jr. ..... Plt. 88

*Primary Examiner*—Howard J. Locker

*Attorney, Agent, or Firm*—Foley & Lardner

[57] ABSTRACT

A new cultivar of Guzmania named 'Twilight', having an inflorescence comprised of deep red bracts and yellow flowers, elongated compound inflorescence, vigorous and tall growth habit, and long, relatively wide leaves.

2 Drawing Sheets

The present invention relates to a new and distinct cultivar of Guzmania, a genus within the family bromeliaceae hereinafter referred to by the cultivar name, 'Twilight'.

Guzmania comprise a genus of over 100 species of evergreen perennials suitable for cultivation in the home or under glass, or outdoors in warm climates. Guzmania are predominantly epiphytic with a few terrestrial species and are native to the tropics. For the most part the species vary in diameter from 7 to 8 inches to 3 or 4 feet and have rosettes of glossy, smooth edged leaves.

Floral bracts of Guzmania frequently have brilliant colors and may last for many months. The range of flower colors for Guzmania is generally from yellow through orange to bright or flame red, and red-purple.

Guzmania may be advantageously grown as pot plants for greenhouse or home use. Desirably the plants are shaded from direct sunlight and during the spring to autumn period, the central vase-like part of the leaf rosette is desirably filled with water.

Guzmania is native to tropical Central and South America. Leaves of the Guzmania are usually formed as basal rosettes which are stiff and entire and in several vertical ranks. Guzmania normally have terminal spikes or panicles which are often bracted with petals united in a tube about as long as the calyx. The ovary is superior and the seeds plumose.

Asexual propagation of Guzmania can be from offshoots produced by the plant which may then be rooted. The resulting plantlets are detached from the mother plant and may be potted up in a suitable growing mixture. Propagation by tissue culture is also extensively practiced and is more efficient for commercial propagation.

The new cultivar 'Twilight' is a product of a planned breeding program and was originated by the inventor from a cross made during such a program in Assendelft, The Netherlands, in 1977. The male, or pollen parent was an unnamed selection from *Guzmania dissitilfora* identified by Code No. 339,005, and the female, or seed parent was an unnamed selection from *Guzmania variegata*, identified by Code No. 339,100. The selection comprising the new variety was chosen after commencement of flowering of the progeny in 1979, and subsequent and continuous asexual propagation has demonstrated that the combination of characteristics as herein disclosed for the new cultivar 'Twilight' are firmly fixed and are retained through successive generations of asexual reproduction.

'Twilight' is particularly characterized by its:

1. Unique compound elongated inflorescence, with the branches extending outwardly and alternately from the main stalk.
2. Solid, tall growth habit.
3. Relatively dark red bract inflorescence with yellow flowers.
4. Long, relatively wide leaves.
5. Long, lasting inflorescence.
6. Floriferous habit.

The new cultivar appears similar to the cultivar 'Marlebeca' due to the red bract-yellow flower of 'Marlebeca'. However, 'Twilight' is distinguished from 'Marlebeca' by its darker inflorescence (bracts) which is longer lasting, its broader and more cascading leaves, and by its more vigorous and large growth habit.

'Twilight' has not been tested under all available environmental conditions and the phenotype may vary with variations in environmental conditions such as temperature, light intensity, day length and humidity. The following observations, measurements and descriptions are based on the growing of 'Twilight' under greenhouse conditions in Assendelft, The Netherlands.

The accompanying color photographic drawings show typical characteristics of 'Twilight', with colors being as true as possible with illustrations of this type. Sheet 1 comprises a perspective view of a full plant with floral bracts. Sheet 2 comprises an enlarged showing of the floral bracts and inflorescence. The photograph comprising sheet 1 is believed to closely depict inflorescence and foliage colors, the correct values for which are noted below. In the enlarged photograph comprising sheet 2, the bract color does not precisely correspond to the true color as described below, but sheets 1 and 2 together are believed to constitute an acceptable showing of true color.

In the following description, color references are made to The Royal Horticultural Society Colour Chart (R.H.S.).

The following traits have been repeatedly observed and in combination distinguish 'Twilight' as a new and distinct cultivar.

I. Plant:

*Form.*—Funnel form rosette.

*Height.*—Approximately 70 cm high at the time of flowering.

*Growth habit.*—Stemless.

*Main stalk (scape).*—Strong and erect; color varies extensively from base to inflorescence; near inflorescence the stalk color is 53A, a deep-red similar to bract color; proceeding toward the base, there is some green showing through the stalk bracts, with the lower stalk bracts (approximately the lower half of the main stock) having tips or ends which are the same green color as the foliage; the main color of the stalk becomes more grey-purple from inflorescence toward the base, with colors 184A and 185A being well represetned; red, grey-purple and green colors will vary depending on temperature, light, fertilizer, and age of plant.

II. Foliage:

*Size of leaf.*—Approximately 50 cm long.

*Shape of leaf.*—Linear — lanceolate.

*Surface texture.*—Smooth.

*Variegation.*—None.

*Orientation.*—Leaves extend away from main stalk and gently cascade to expose the long main stalk and the intense red inflorescence, and to provide a full round appearance.

*Color.*—Upperside, near R.H.S. 147A. Underside, near R.H.S. 147B. Near base, R.H.S. 59A.

III. Bracts:

*Length.*—Primary bracts approximately 5.5 cm; scape bracts approximately 8 cm; and floral bracts approximately 2.5 cm.

*Width.*—At the base, primary and scape bracts are approximately 4 cm, and floral bracts 1.5 cm.

*General shape.*—Ovate-lanceolate.

*Number.*—Approximately 11 primary bracts.

*Texture.*—Smooth.

*Margin.*—Entire.

*Color.*—Outer surface, R.H.S. 53B; inner surface, R.H.S. 53C.

IV. Flowers:

*Borne.*—On erect stalks.

*Shape of inflorescence.*—Compound, alternately from main stalk.

*Length of inflorescence on stalk.*—Approximately 25 cm.

*Individual petals.*—(1) Length: Approximately 3.5 cm long, of which 3 cm is disposed within the sepals which are hidden for 2.5 cm behind the floral bracts. (2) Diameter: Approximately 0.4 cm. (3) Quantity: Approximately 100 flowers divided over approximately 11 branches, depending on the size of plant. (4) Color: R.H.S. 6B.

*Time of blooming.*—In a fully grown plant, flowers start approximately 20 weeks after induction, and blooming can be scheduled for any time of the year.

*Duration of blooms.*—Each flower blooms 1 day and the total duration of blooming is about 6 weeks.

V. Reproductive organs:

*Ovaries.*—Superior.

*Stamens.*—6 in number.

VI. Seed characteristics: Sterile hybrid, therefore no seed.

I claim:

1. A plant of a new and distinct cultivar of Guzmania plant named 'Twilight', as illustrated and described.

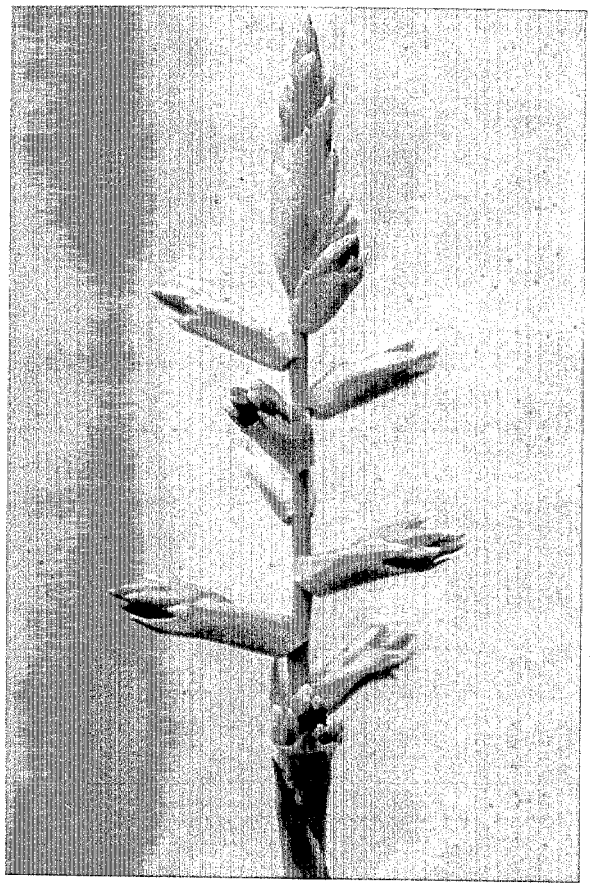

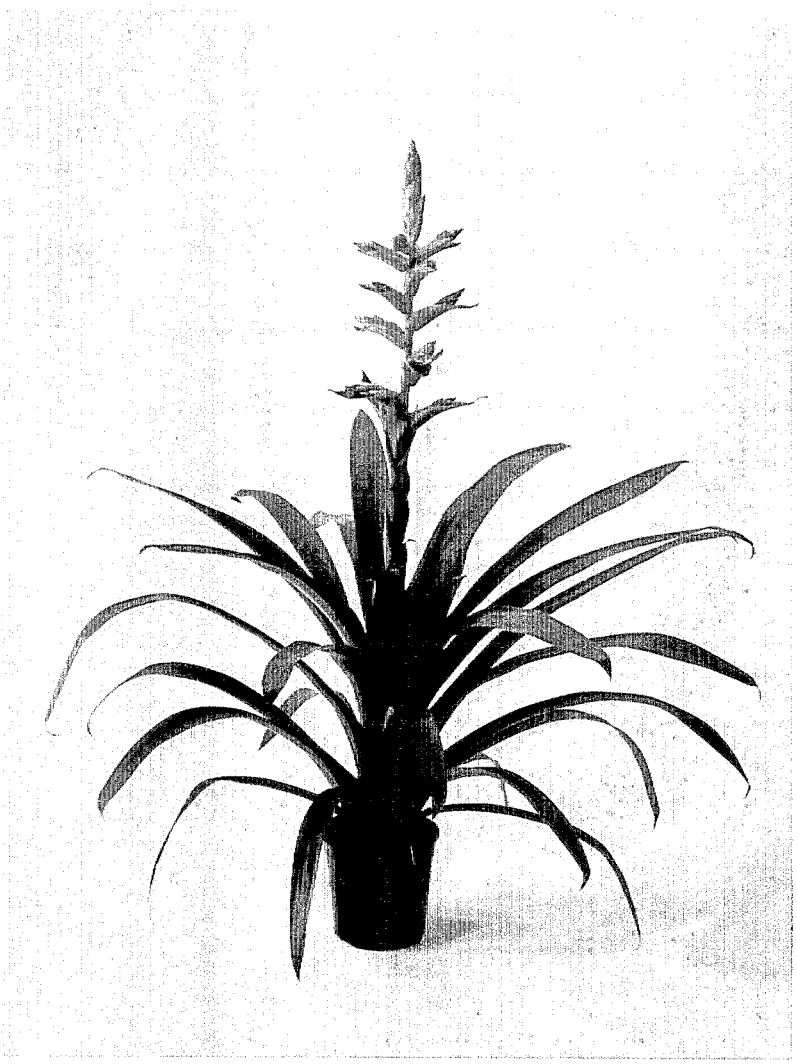

* * * * *